US012697476B2

(12) United States Patent
Blanchard et al.

(10) Patent No.: US 12,697,476 B2
(45) Date of Patent: Aug. 4, 2026

(54) INSTRUMENT ADVANCEMENT DEVICE

(71) Applicant: Becton, Dickinson and Company, Franklin Lakes, NJ (US)

(72) Inventors: Curtis H. Blanchard, Herriman, UT (US); Adam J. Boud, Bluffdale, UT (US); John M. Lackey, West Valley City, UT (US); Megan S. Scherich, Salt Lake City, UT (US); Shaun Staley, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 538 days.

(21) Appl. No.: 18/237,165

(22) Filed: Aug. 23, 2023

(65) Prior Publication Data

US 2024/0066278 A1    Feb. 29, 2024

Related U.S. Application Data

(60) Provisional application No. 63/400,503, filed on Aug. 24, 2022.

(51) Int. Cl.
| | |
|---|---|
| *A61M 39/04* | (2006.01) |
| *A61B 5/15* | (2006.01) |
| *A61M 25/09* | (2006.01) |
| *A61M 39/02* | (2006.01) |

(52) U.S. Cl.
CPC ....... *A61M 39/04* (2013.01); *A61B 5/150992* (2013.01); *A61M 25/09* (2013.01); *A61M 2025/09066* (2013.01); *A61M 2039/0258* (2013.01); *A61M 2039/027* (2013.01); *A61M 2039/0273* (2013.01)

(58) Field of Classification Search
CPC .................. A61M 39/04; A61M 25/09; A61M 2025/09066; A61M 2039/0258; A61M 2039/027; A61M 2039/0273; A61M 2039/0294; A61M 2039/066; A61M 39/0693; A61M 2025/0079; A61M 2025/09116; A61B 5/150992
See application file for complete search history.

(56) References Cited

U.S. PATENT DOCUMENTS

| | | | |
|---|---|---|---|
| 2015/0224267 A1* | 8/2015 | Farrell | ................. A61M 5/326 |
| | | | 604/263 |
| 2017/0361071 A1 | 12/2017 | Belson | |
| 2018/0140240 A1 | 5/2018 | Bullington et al. | |
| 2019/0321590 A1* | 10/2019 | Burkholz | ............... A61M 5/14 |

(Continued)

*Primary Examiner* — Bhisma Mehta
*Assistant Examiner* — Marissa Taylor
(74) *Attorney, Agent, or Firm* — The Webb Law Firm

(57) ABSTRACT

An instrument advancement device includes an access connector configured to be connected to a vascular access device, a primary lumen in fluid communication with the access connector, an instrument received within the primary lumen and having a retracted position and an extended position, an advancement member configured to move the instrument between the retracted position and the extended position, and a lumen seal received within the primary lumen and connected to the instrument. The lumen seal defines a space between the lumen seal and the primary lumen when the instrument is in the retracted portion. The lumen seal engages the primary lumen when the instrument is in the advanced position.

20 Claims, 15 Drawing Sheets

(56)  References Cited

U.S. PATENT DOCUMENTS

| 2021/0213268 | A1* | 7/2021 | Scherich ......... | A61M 25/09041 |
| 2021/0228127 | A1 | 7/2021 | Burkholz et al. | |
| 2021/0290126 | A1 | 9/2021 | Burkholz et al. | |
| 2021/0290905 | A1 | 9/2021 | Harding et al. | |
| 2021/0393924 | A1 | 12/2021 | Burkholz et al. | |
| 2021/0402152 | A1 | 12/2021 | Burkholz et al. | |
| 2022/0218252 | A1* | 7/2022 | Blanchard ........ | A61B 5/150992 |
| 2022/0218955 | A1 | 7/2022 | Scherich et al. | |
| 2022/0313958 | A1 | 10/2022 | Harding et al. | |
| 2022/0379074 | A1 | 12/2022 | Burkholz et al. | |
| 2023/0001144 | A1 | 1/2023 | Burkholz et al. | |

* cited by examiner

INSTRUMENT ADVANCEMENT DEVICE

CROSS-REFERENCE TO RELATED APPLICATION

The present application claims priority to U.S. Provisional Application No. 63/400,503, entitled "Instrument Advancement Device" filed Aug. 24, 2022, the entire disclosure of which is hereby incorporated by reference in its entirety.

BACKGROUND OF THE INVENTION

Field of the Invention

The present disclosure relates to an instrument advancement device.

Description of Related Art

Catheters are frequently utilized to administer fluids into and out of the body. Patients in a variety of settings, including in hospitals and in home care, receive fluids, pharmaceuticals, and blood products via a vascular access device inserted into a patient's vascular system. Catheters of various types and sizes have been used extensively in a variety of procedures including, but not limited to, treating an infection, providing anesthesia or analgesia, providing nutritional support, treating cancerous growths, maintaining blood pressure and heart rhythm, and many other clinical uses. A common vascular access device is a plastic catheter that is inserted into a patient's vein. The catheter length may vary from a few centimeters for peripheral access to many centimeters for central access. The catheter is commonly incorporated into a catheter adapter to aid in the ease of use, accessibility, and utility of the catheter. A catheter adapter may be adapted to house one end of the catheter such that one end of the catheter is supported by the catheter adapter and the body and tip of the catheter extends beyond a first end of the catheter adapter. A catheter adapter generally further includes a second end adapted to receive additional infusion components for use with the catheter. For example, the second end of a catheter adapter may include a set of threads for attaching an intravenous line or for coupling a syringe to the catheter adapter thereby providing access to the patient's vasculature via the attached catheter.

The catheter may be inserted transcutaneously. When inserted transcutaneously, the insertion of the catheter is commonly aided by an introducer needle. The introducer needle is commonly housed inside the lumen of the catheter such that the gauge of the needle approximates the inner diameter of the catheter. The needle is positioned within the catheter such that the needle tip extends beyond the tip of the catheter whereby the needle is used to penetrate the patient's vein and provide an opening for insertion of the catheter.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal, fluid infusion, or probe access.

Blood withdrawal or infusion using the catheter may be difficult for several reasons, particularly when a dwelling time of the catheter within the patient is more than one day. For example, when the catheter is left inserted in the patient for a prolonged period of time, the vein and catheter may be more susceptible to narrowing, collapse, kinking, blockage by debris (e.g., fibrin, platelet clots, or thrombus), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is desired, an additional needle stick is used to provide vein access for blood collection, which may be painful for the patient and result in higher material costs.

SUMMARY OF THE INVENTION

In one aspect or embodiment, an instrument advancement device includes an access connector configured to be connected to a vascular access device, a primary lumen in fluid communication with the access connector, an instrument received within the primary lumen and having a retracted position where a distal end of the instrument is positioned within the primary lumen or the access connector, and an extended position where the distal end of the instrument extends beyond a distal end of the primary lumen and the access connector, an advancement member configured to be grasped by a healthcare technician, where movement of the advancement member moves the instrument between the retracted position and the extended position, and a lumen seal received within the primary lumen and connected to the instrument. The lumen seal defines a space between the lumen seal and the primary lumen when the instrument is in the retracted position and the lumen seal engages the primary lumen when the instrument is in the advanced position.

The lumen seal may engage a narrowed portion of the primary lumen when the instrument is in the advanced position, with the narrowed portion having a smaller inner diameter than a remaining portion of the primary lumen. The lumen seal may include a first portion and a second portion, with the first portion larger in diameter than the second portion. The lumen seal may include a distal tapered portion. The lumen seal may include an elastomeric material. The lumen seal may define a central opening, where a portion of the instrument passes through the central opening.

The instrument may include a flow tube and a guidewire positioned distally of the flow tube. The guidewire may include a helical coil portion. The device may include a wedge member defining a central passage, where the central passage of the wedge member receives a portion of the flow tube and a portion of the guidewire, and where the guidewire and the flow tube are attached to the wedge member. The advancement member may be configured to move along an outer surface of the primary lumen, where the advancement member engages the wedge member from outside of the primary lumen to move the instrument between the retracted position and the extended position. The lumen seal may define a central opening that receives a portion of the wedge member, where the lumen seal is attached to the wedge member. The guidewire may extend through the lumen seal, where a portion of the flow tube is received within the central opening of the lumen seal.

The device may include a cannula configured to pierce the lumen seal when the instrument is moved to the advanced position, where a flow path defined by the instrument is sealed until the cannula pierces the lumen seal. The device may include a vent plug positioned within the primary lumen and positioned proximally relative to the advancement member, where a flow path to the vent plug extends from the access connector, through the primary lumen, and between the primary lumen and the lumen seal. The vent plug may be a hydrophilic vent and configured to allow the primary lumen to receive a waste blood volume.

When the access connector is connected to an integrated catheter, the flow tube may be configured to be received within at least a portion of the integrated catheter.

At least a portion of the primary lumen may have an asymmetrical transverse cross-section defining a larger diameter portion and a smaller diameter portion, with a portion of the guidewire received within the smaller diameter portion. The smaller diameter portion may be configured to support the guidewire when the instrument is moved from the retracted position to the advanced position.

The device may include a flow restrictor configured to reduce risk of hemolysis. The flow restrictor may be a tubular insert received within at least a portion of the access connector.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE INVENTION

Figure 1:
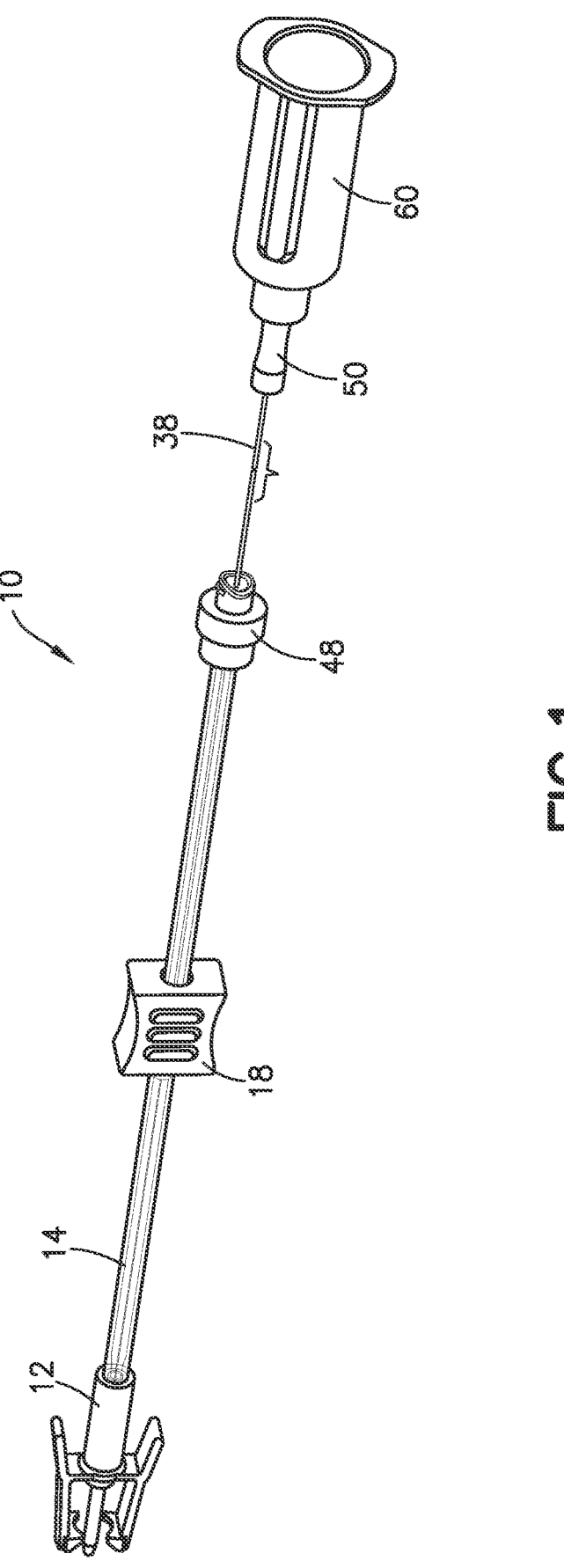
FIG. 1 is a perspective view of an instrument advancement device according to one aspect or embodiment of the present application, showing the device with an access device.
Figures 2, 3:
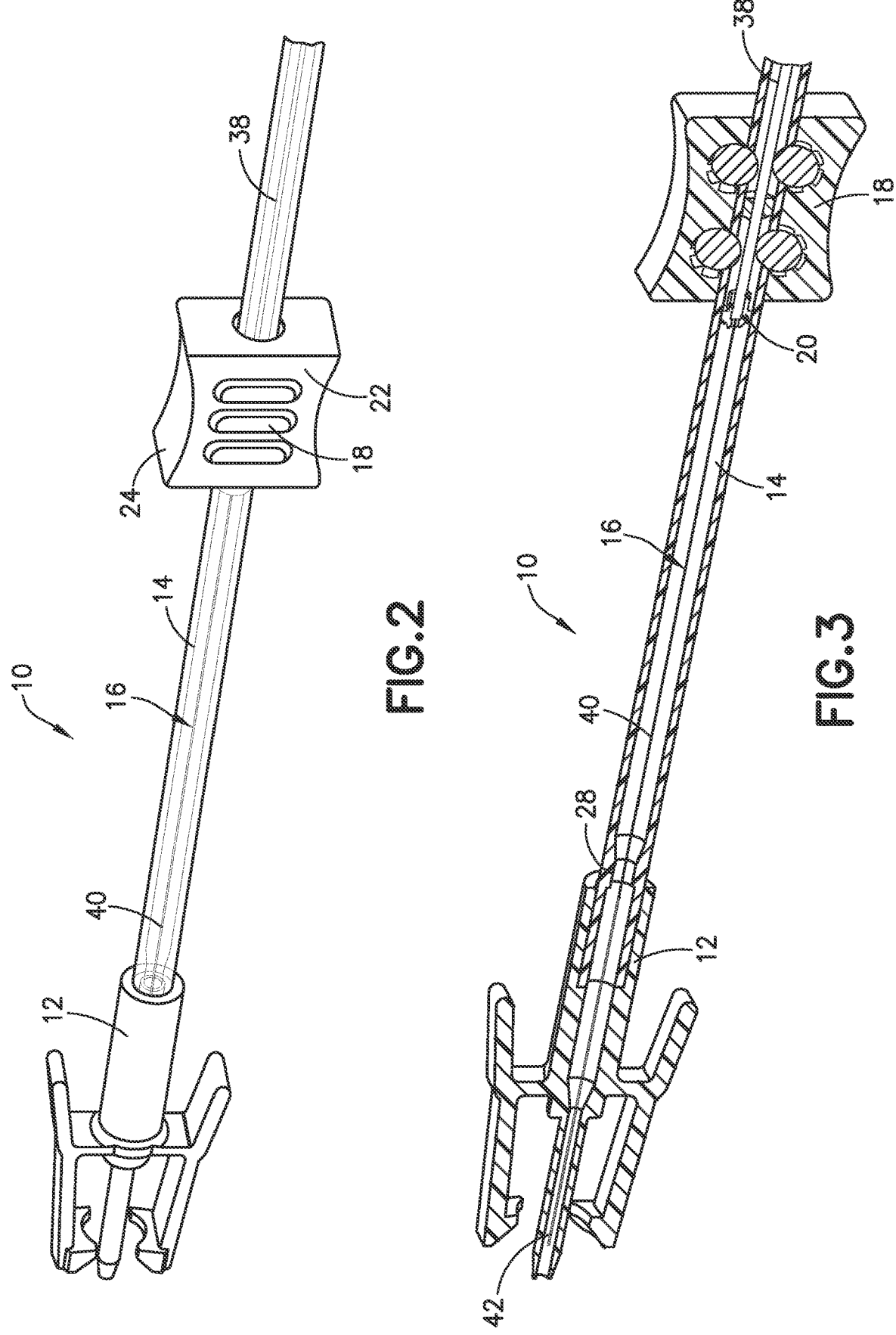
FIG. 2 is a perspective view of the device of FIG. 1, showing a retracted positon of an instrument.
FIG. 3 is a cross-sectional view of the device of FIG. 1, showing a retracted position of an instrument.

Spatial or directional terms, such as "left", "right", "inner", "outer", "above", "below", and the like, are not to be considered as limiting as the invention can assume various alternative orientations.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less.

The terms "first", "second", and the like are not intended to refer to any particular order or chronology, but refer to different conditions, properties, or elements.

As used herein, "at least one of" is synonymous with "one or more of". For example, the phrase "at least one of A, B, and C" means any one of A, B, or C, or any combination of any two or more of A, B, or C. For example, "at least one of A, B, and C" includes one or more of A alone; or one or more of B alone; or one or more of C alone; or one or more of A and one or more of B; or one or more of A and one or more of C; or one or more of B and one or more of C; or one or more of all of A, B, and C.

Referring to FIGS. 1-9, in one aspect or embodiment, an instrument advancement device 10 includes an access connector 12 configured to be connected to a vascular access device, a primary lumen 14 in fluid communication with the access connector 12, an instrument 16 received within the primary lumen 14, an advancement member 18 configured to be grasped by a healthcare technician, and a lumen seal 20 received within the primary lumen 14 and connected to the instrument 16. The instrument 16 has a retracted position (FIG. 3), where a distal end of the instrument 16 is positioned within the primary lumen 14 or the access connector 12, and an extended position (FIG. 8), where the distal end of the instrument 16 extends beyond a distal end of the primary lumen 14 and the access connector 12. Movement of the advancement member 18 moves the instrument 16 between the retracted position and the extended position. The lumen seal 20 defines a space between the lumen seal 20 and the primary lumen 14 when the instrument 16 is in the retracted position. The lumen seal 20 engages the primary lumen 14 when the instrument 16 is in the advanced position. The instrument advancement device 10 is configured to be connected to a vascular access device, such as a catheter, and enables blood draw via the vascular access device by extending the instrument 16 into a patient's vasculature and providing access beyond thrombus, valves, or other obstructions. By providing the space between the lumen seal 20 and the primary lumen 14 when the instrument 16 is in the retracted position and engaging the primary lumen 14 when the instrument 16 is in the advanced position, the force required to move the advancement member 18 and the instrument 16 is minimized while still allowing the flow path through the primary lumen 14 to be sealed when the instrument 16 is moved to the advanced position.

Figure 6:
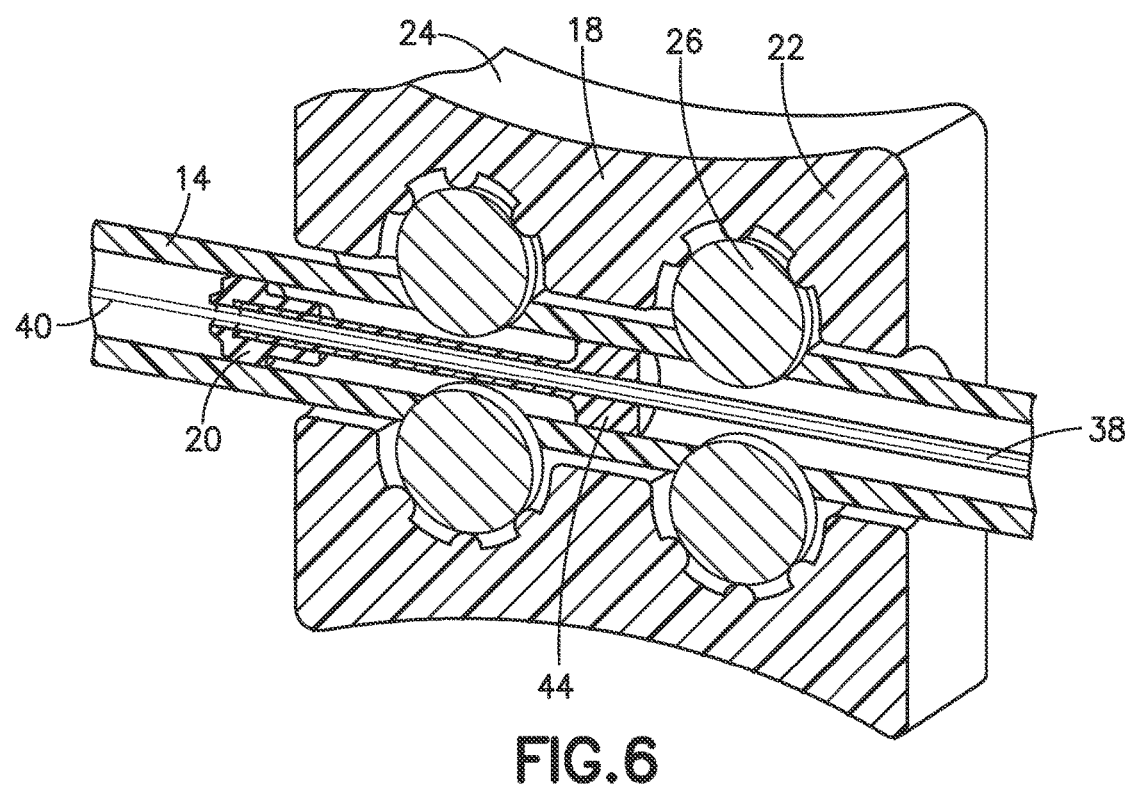
FIG. 6 is a partial cross-sectional view of the device of FIG. 1.

Referring to FIG. 6, for example, the advancement member 18 is configured to move along an outer surface of the primary lumen 14, with the advancement member 18 entirely positioned outside of the primary lumen 14. The advancement member 18 includes a body 22 having gripping surfaces 24 and ball bearings 26, or other suitable features, that engage the outer surface of the primary lumen 14 and allow advancement of the instrument 16 by compressing the primary lumen 14 as discussed in additional detail below. Although the ball bearings 26 are shown extending through the primary lumen 14 in certain figures, the ball bearings 26 do not extend through the primary lumen 14 and only contact or compress the primary lumen 14 externally. The advancement member 18 may be the same or similar to the translation handle shown and described in U.S. Patent Application Publication No. 2021/0290126, which is hereby incorporated by reference in its entirety.

Figures 4, 5:
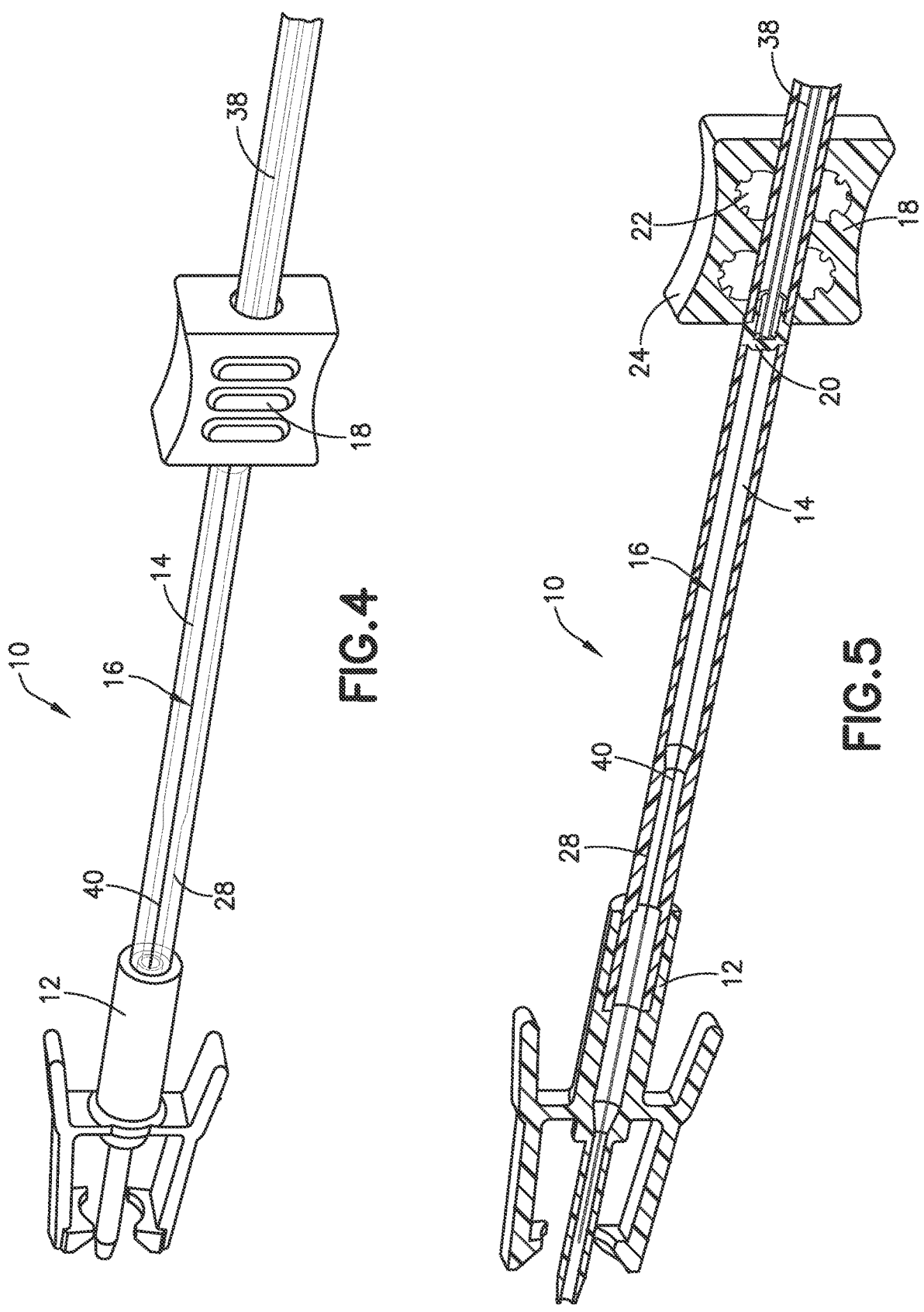
FIG. 4 is a perspective view of an instrument advancement device according to a further aspect or embodiment of the present application, showing a retracted position of an instrument.
FIG. 5 is a cross-sectional view of the device of FIG. 4, showing a retracted position of an instrument.

Referring to FIGS. 4, 5, 8, and 9, the lumen seal 20 engages a narrowed portion 28 of the primary lumen 14 when the instrument 16 is in the advanced position, with the narrowed portion 28 having a smaller inner diameter than a remaining portion of the primary lumen 14. As shown in FIGS. 4 and 5, in some aspects or embodiments, the narrowed portion 28 is longer than the narrowed portion 28 shown in FIGS. 2 and 3 to allow for additional advancement and retraction of the instrument 16 while in the draw zone, with the lumen seal 20 forming a seal with the primary lumen 14. In one aspect or embodiment, a vacuum draw is applied prior to advancement or retraction of the instrument 16 while in the draw zone. In one aspect or embodiment, the device 10 is fully primed to remove air from the device 10 prior to advancement or retraction of the instrument 16 while in the draw zone.

Referring to FIGS. 6-9, in one aspect or embodiment, the lumen seal 20 includes a first portion 30 and a second portion 32, with the first portion 30 larger in diameter than the second portion 32. The lumen seal 20 also includes a distal tapered portion 34. In some aspects or embodiments, the lumen seal 20 is formed from an elastomeric material, such as polyisoprene, although other suitable materials may be utilized. The lumen seal 20 and/or instrument 16 may include a lubricant to facilitate sliding between the components. The lumen seal 20 defines a central opening 36, with a portion of the instrument 16 passing through the central opening 36. As shown, in one aspect or embodiment, the instrument 16 includes a flow tube 38 and a guidewire 40 positioned distally of the flow tube 38. The guidewire 40 also may include a helical coil portion 42 at a distal end of the guidewire 40. Other suitable arrangements for the instrument 16, however, may be utilized, such as a flow tube that extends a full length of the instrument 16, a guidewire extending the full length of the instrument 16, or a sensor deployment instrument.

Figure 7:
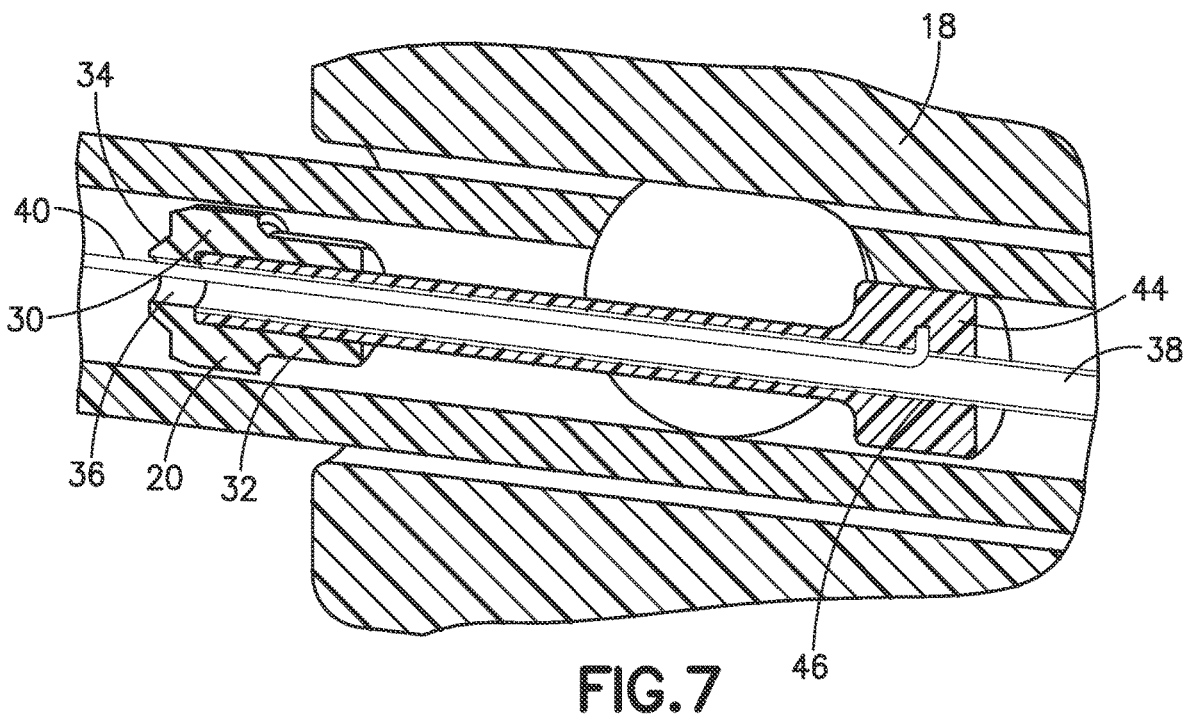
FIG. 7 is a partial cross-sectional view of the device of FIG. 1.
Figure 8:
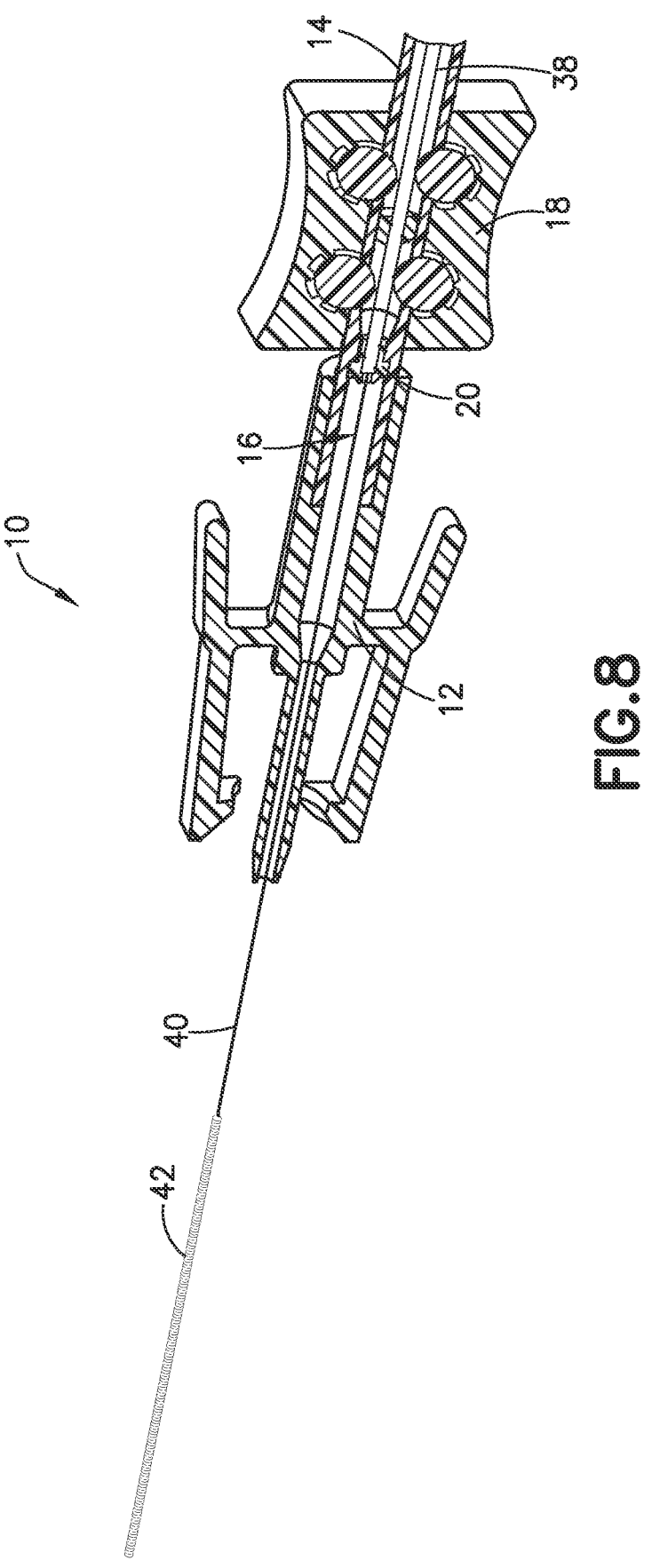
FIG. 8 is a partial cross-sectional view of the device of FIG. 1, showing an advanced position of an instrument.
Figure 9:
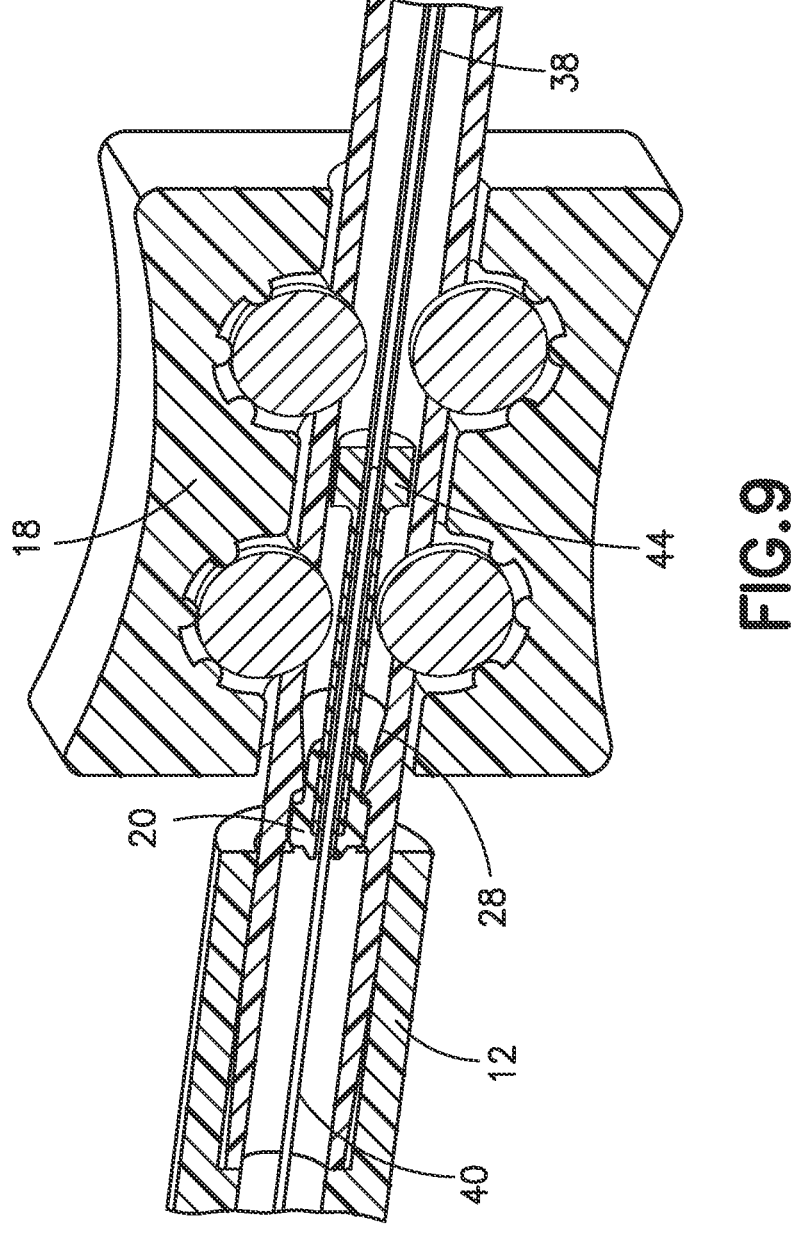
FIG. 9 is a partial cross-sectional view of the device of FIG. 1, showing an advanced position of an instrument.

Referring to FIG. 7, the device 10 further includes a wedge member 44 defining a central passage 46, with the central passage 46 of the wedge member 44 receiving a portion of the flow tube 38 and a portion of the guidewire 40. The guidewire 40 and the flow tube 38 are attached to the wedge member 44. In one aspect or embodiment, the guidewire 40 and/or flow tube 38 may be bonded or attached to the wedge member 44 via adhesive, overmolding, or other suitable techniques. A proximal end of the guidewire 40 may extend through the flow tube 38 and into the wedge member 44. The advancement member 18 engages the wedge member 44 from outside of the primary lumen 14 to move the instrument 16 between the retracted position and the extended position. The central opening 36 of the lumen seal 20 receives a portion of the wedge member 44 and the lumen seal 20 is attached to the wedge member 44. The lumen seal 20 may be attached to the wedge member 44 via adhesive, overmolding, or other suitable techniques. The guidewire 40 extends through the lumen seal 20, with a portion of the flow tube 38 received within the central opening 36 of the lumen seal 20. When the instrument 16 is moved to the advanced position and with the lumen seal 20 engaged with the primary lumen 14, the access connector 12 is no longer in fluid communication with the primary lumen 14 and only in fluid communication with the flow tube 38.

Referring to FIG. 1, a proximal end of the primary lumen 14 is connected to a needle-free connector 48, with the flow tube 38 of the instrument 16 extending through the needle-free connector 48. A proximal end of the flow tube 38 includes a connector 50 configured to be connected to an access device 60, which may be a BD Vacutainer® Luer-Lok™ access device. An evacuated container (not shown) may be inserted into the access device 60 to facilitate blood draw via the instrument 16.

Figures 10, 11:
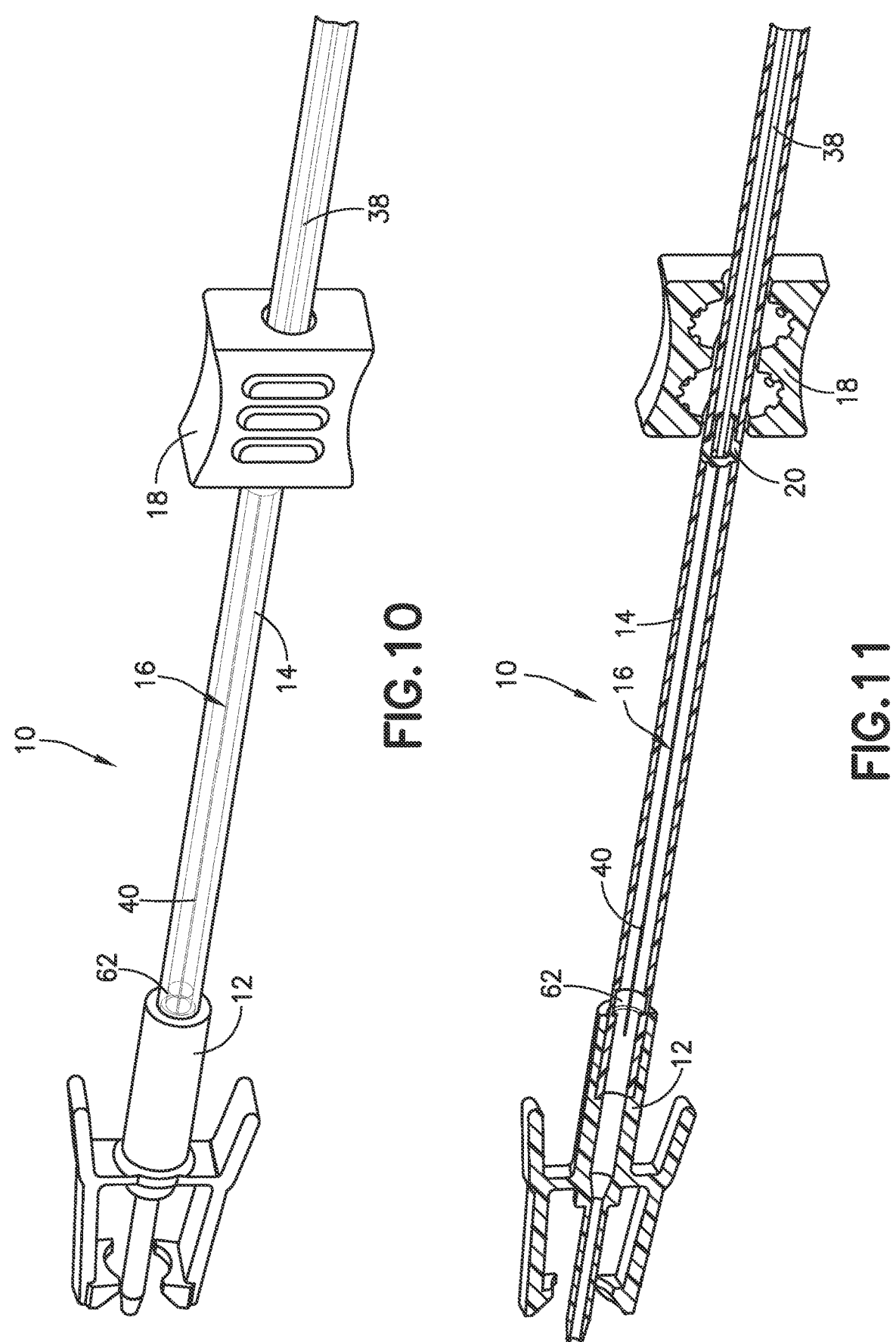
FIG. 10 is a perspective view of an instrument advancement device according to a further aspect or embodiment of the present application, showing a retracted position of an instrument.
FIG. 11 is a cross-sectional view of the device of FIG. 10, showing a retracted position of an instrument.
Figures 12, 13:
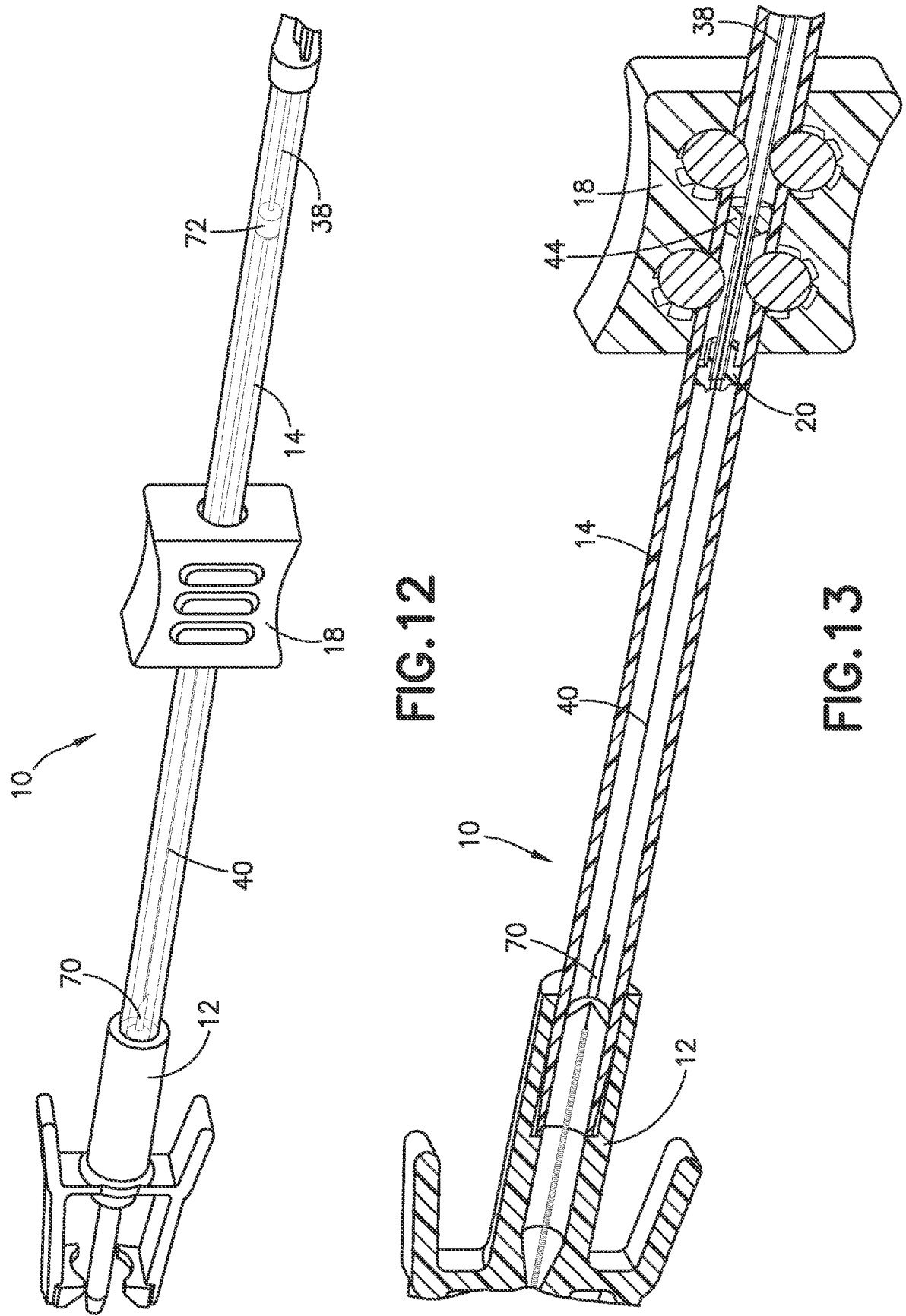
FIG. 12 is a perspective view of an instrument advancement device according to a further aspect or embodiment of the present application, showing a retracted position of an instrument.
FIG. 13 is partial cross-sectional view of the device of FIG. 12, showing a retracted position of an instrument.
Figures 14, 15:
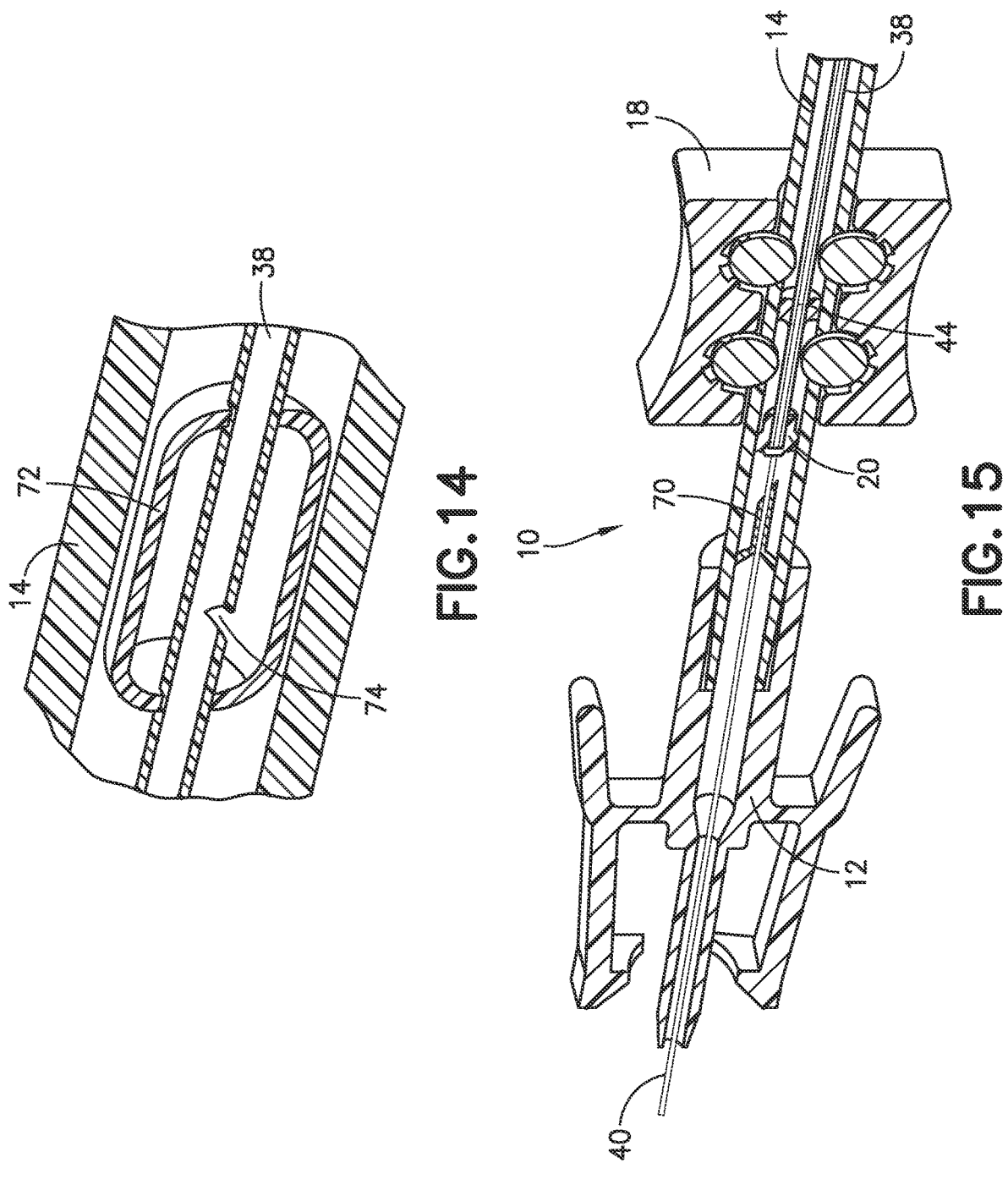
FIG. 14 is a partial cross-sectional view of the device of FIG. 12, showing a vent plug according to one aspect or embodiment of the present application.
FIG. 15 is a partial cross-sectional view of the device of FIG. 12, showing a partially advanced position of an instrument.
Figures 16, 17:
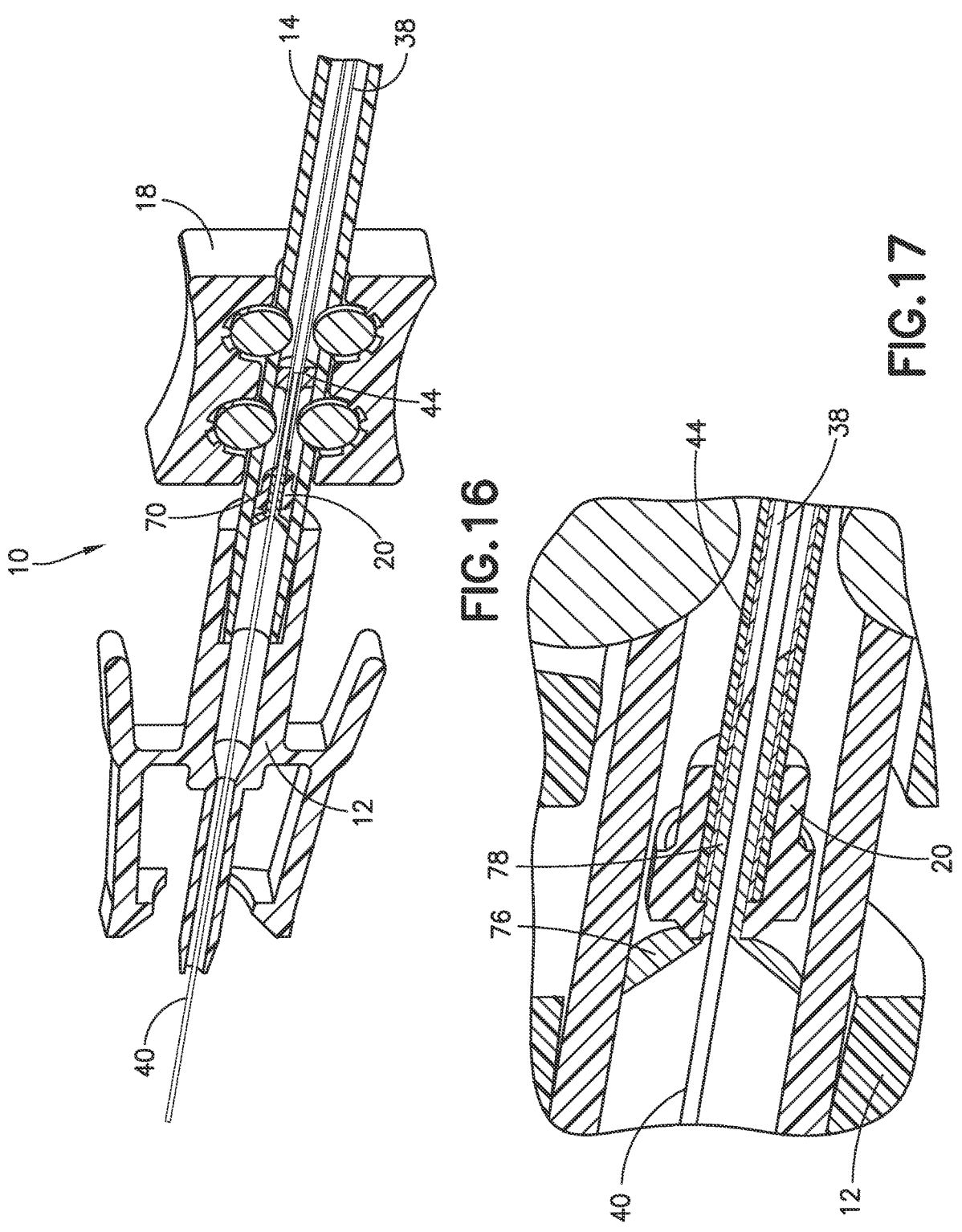
FIG. 16 is a partial cross-sectional view of the device of FIG. 12, showing an advanced position of an instrument.
FIG. 17 is a partial cross-sectional view of the device of FIG. 12, showing an advanced position of an instrument.

Referring to FIGS. 10 and 11, in one aspect or embodiment, instead of providing the narrowed portion 28, the primary lumen 14 has a catch or clip 62 configured to secure the lumen seal 20 after the instrument 16 is fully advanced to the advanced position. The catch or clip 62 may have a larger inner diameter compares to the rest of the primary lumen 14, which enables the lumen seal 20 to be caught and locked into the catch or clip 62 once the lumen seal 20 is advanced and remains within the catch or clip 62 once the advancement member 18 is retracted. The lumen seal 20 may have an interference fit with the primary lumen 14, with the instrument 16 being withdrawn through the lumen seal 20. Although requiring a higher force during advancement of the instrument 16, the instrument 16 is not subject to such forces, except on withdrawal while the instrument 16 is in tension, thereby minimizing buckling. Fluid communication is present from the access connector 12 to the primary lumen 14 until the advancement member 18 is moved to the advanced position. Once the advancement member 18 is advanced, fluid communication only occurs between the access connector 12 and the flow tube 38.

Referring to FIGS. 12-17, in a further aspect or embodiment, the instrument advancement device 10 includes a cannula 70 configured to pierce the lumen seal 20 when the instrument 16 is moved to the advanced position. A flow path defined by the flow tube 38 of the instrument 16 is sealed until the cannula 70 pierces the lumen seal 20. A vent plug 72 is positioned within the primary lumen 14 and positioned proximally relative to the advancement member 18, with the flow tube 38 of the instrument 16 defining a vent opening 74 in fluid communication with the vent plug 72. A flow path to the vent plug 72 extends from the access connector 12, through the primary lumen 14, and between the primary lumen 14 and the lumen seal 20. In some aspects or embodiments, the vent plug 72 is a hydrophilic vent, such as a porex flow plug or similar occluding device. The vent plug 72 is configured to allow the primary lumen 14 to receive a waste blood volume, which is configured to eliminate the need for a waste tube draw. If additional suction of an evacuated tube or syringe is required to enable the blood to flow at a desired rate during the waste process, an oversized primary evacuated tube or a syringe with a withdraw plunger could be used to draw the air, then after the cannula 70 pierces the lumen seal 20, the needed volume of blood could be collected into the remaining capacity of the evacuated tube or the syringe. The flow of blood is stopped by the vent plug 72 with the final advancement of the instrument 16 causing the cannula 70 to pierce the lumen seal 20 and provide an open fluid path through the flow tube 38 of the instrument 16, thereby providing a fluid path that is less likely to include contaminants. In some aspects or embodiments, rather than providing the vent plug 72, the needle-free connector 48 could include a hydrophilic vent, thereby eliminating the need for adding the vent opening 74 in the flow tube 38. The waste draw into the primary lumen 14 may be aided by using an evacuated tube. As shown more clearly in FIG. 17, the cannula 70 includes a flange portion 76 attached to the primary lumen 14 and/or the access connector 12 and an extension portion 78 having a sharp distal end. The guidewire 40 is configured to extend through the cannula 70 when the instrument 16 is moved to the advanced position, which forms a fluid path between the guidewire 40 and the cannula 70.

Figures 18, 19, 20:
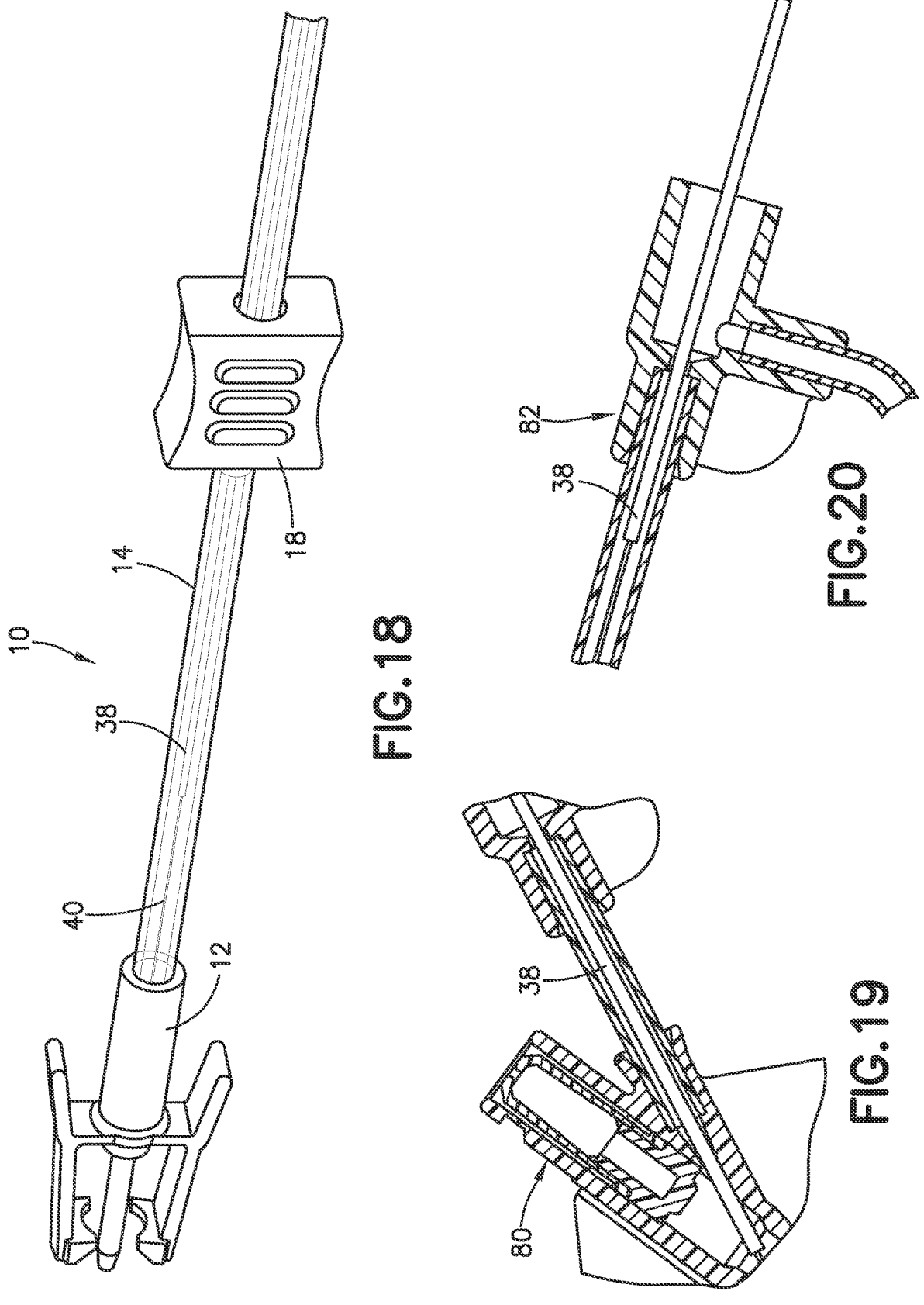
FIG. 18 is a perspective view of an instrument advancement device according to a further aspect or embodiment of the present application, showing a retracted position of an instrument.
FIG. 19 is a partial cross-sectional view of the device of FIG. 18, showing an instrument received within an integrated catheter.
FIG. 20 is a partial cross-sectional view of the device of FIG. 18, showing an instrument received within a T-connector.
Figure 22:
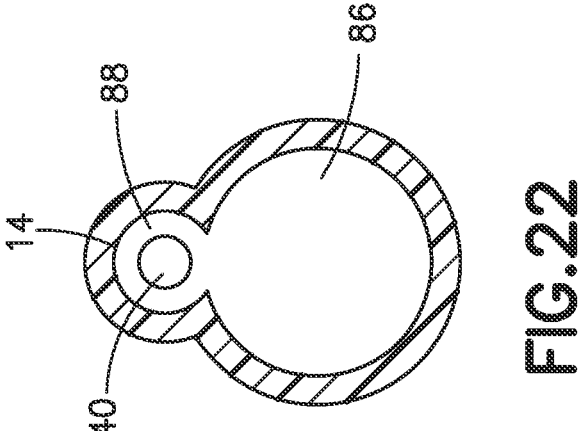
FIG. 22 is a schematic view of the instrument of FIG. 21.
Figure 21:
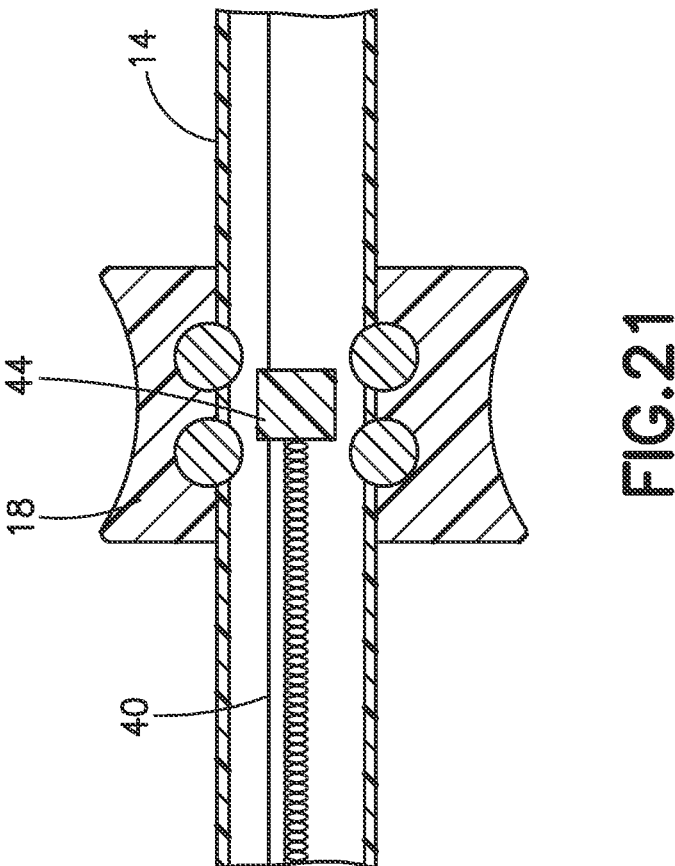
FIG. 21 is a schematic view of an advancement member and instrument according to a further aspect or embodiment of the present application.
Figure 23:
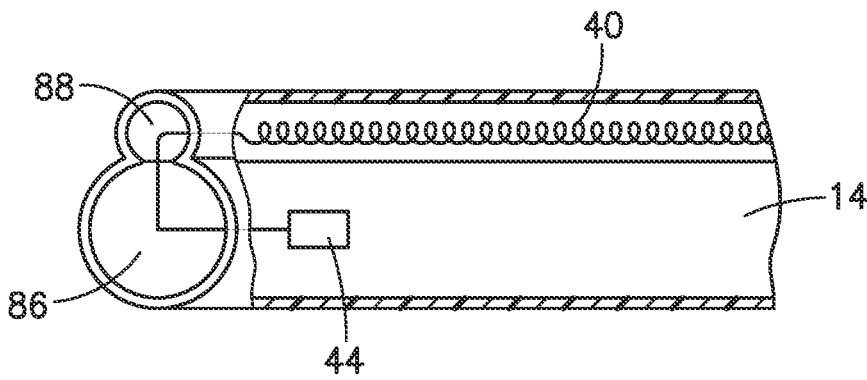
FIG. 23 is a schematic view of the advancement member and instrument of FIG. 21, showing a non-buckling condition of the instrument.
Figure 24:
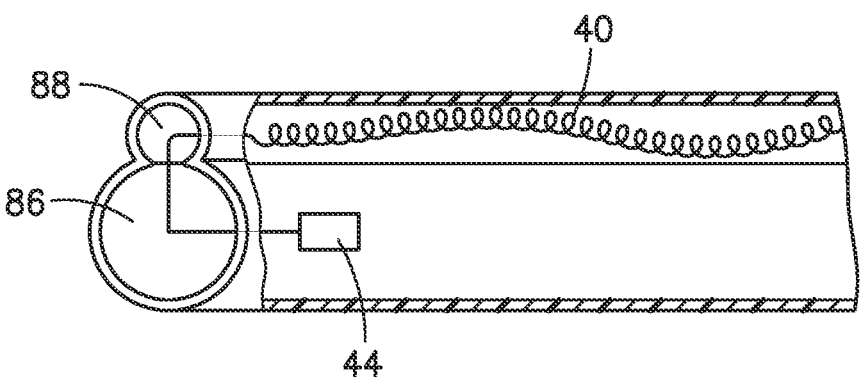
FIG. 24 is a schematic view of the advancement member and instrument of FIG. 21, showing a buckling condition of the instrument.
Figure 25:
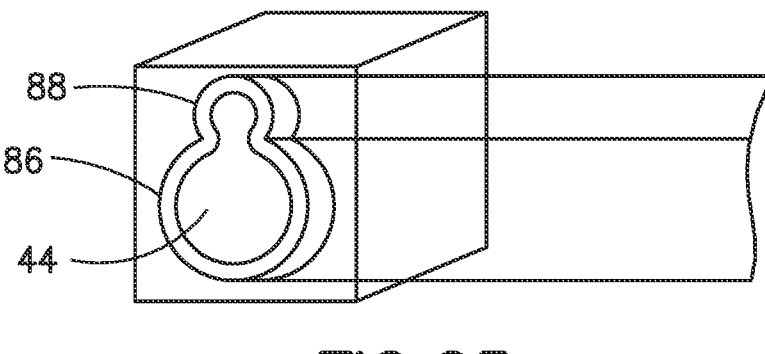
FIG. 25 is a schematic view of the advancement member and instrument of FIG. 21.

Referring to FIGS. 18-20, in one aspect or embodiment, the flow tube 38 of the instrument 16 extends distally relative to the lumen seal 20, but does not extend the full length of the instrument 16. With such an arrangement, as shown in FIG. 19, when the access connector 12 is connected to an integrated catheter 80, the flow tube 38 is configured to be received within at least a portion of the integrated catheter 80. Similarly, as shown in FIG. 20, the flow tube 38 of the instrument 16 is configured to extend beyond a T-connector 82. Providing the flow tube 38 distal to the lumen seal 20 is configured to reduce the mixing of fluid within the integrated catheter 80 or the T-connector 82, thereby preventing contamination of the T-connector 82 and the integrated catheter 80. The flow tube 38 may form a seal with a portion of the T-connector 82 or with the wedge member 44 to ensure that mixing, dilution, and/or contamination does not migrate from those areas.

Referring to FIGS. 21-25, in a further aspect or embodiment, at least a portion of the primary lumen 14 has an asymmetrical transverse cross-section defining a larger diameter portion 86 and a smaller diameter portion 88, with a portion of the guidewire 40 received within the smaller diameter portion 88. The smaller diameter portion 88 is configured to support the guidewire 40 when the instrument 16 is moved from the retracted position to the advanced position and prevent the guidewire 40 from entering the larger diameter portion 86. The asymmetrical transverse cross-section may be provided along the full length of the primary lumen 14, at intermittent location along the length, or only at an end of the primary lumen 14.

Figure 26:
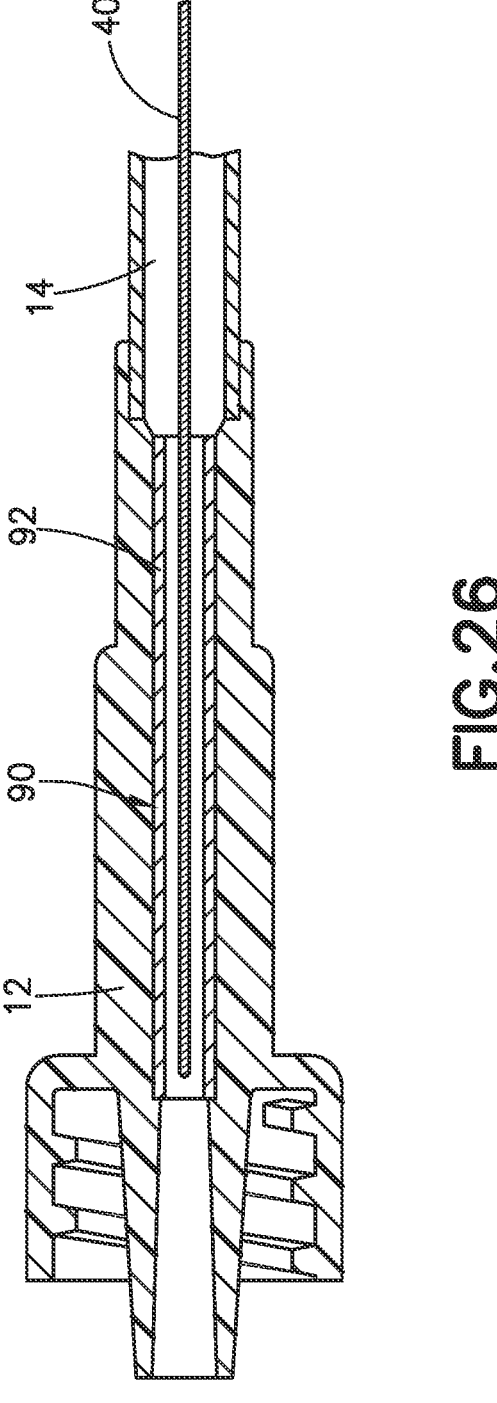
FIG. 26 is a partial cross-sectional view of an instrument advancement device according to a further aspect or embodiment of the present application.

Referring to FIG. 26, in a further aspect or embodiment, the instrument advancement device 10 includes a flow restrictor 90 configured to reduce the risk of hemolysis. The flow restrictor 90 may be a tubular insert 92 received within at least a portion of the access connector 12. The flow restrictor 90 may have a smaller inner diameter than the primary lumen 14, with the guidewire 40 of the instrument 16 configured to extend through the flow restrictor 90. The flow restrictor 90 may be formed from stainless steel, extruded plastic, or other suitable material.

Figure 27:
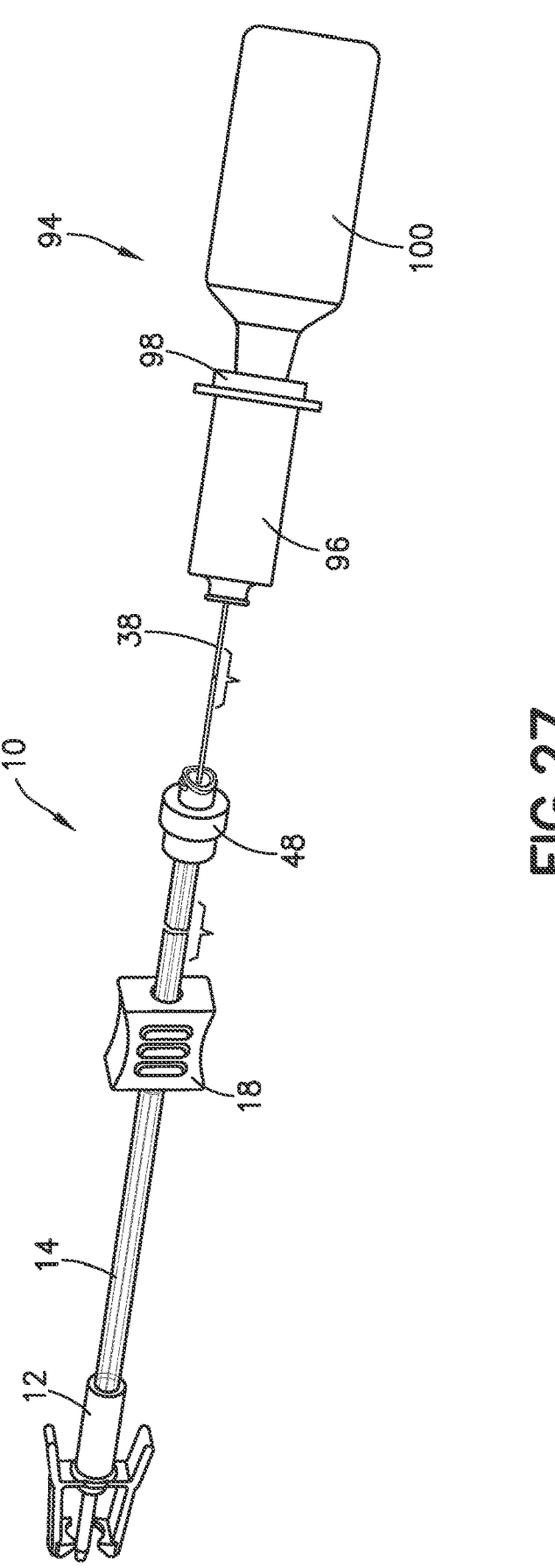
FIG. 27 is perspective view of the device of FIG. 1, showing the device utilized in connection with a blood sample collection system.

Referring to FIG. 27, in some aspects or embodiments, the access device 60 is a blood culture sample collection system 94 including a container holder 96, an adapter 98, and a collection container 100. The blood culture sample collection system 94 is configured to be assembled and sterilized with the collection container 100 in a pre-advancement position, thereby eliminating connection steps and reducing the risk of sample contamination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An instrument advancement device comprising:

an access connector configured to be connected to a vascular access device;

a primary lumen in fluid communication with the access connector;

an instrument received within the primary lumen and having a retracted position where a distal end of the instrument is positioned within the primary lumen or the access connector, and an advanced position where the distal end of the instrument extends beyond a distal end of the primary lumen and the access connector;

an advancement member configured to be grasped by a healthcare technician, wherein movement of the advancement member moves the instrument between the retracted position and the advanced position; and a lumen seal received within the primary lumen and connected to the instrument, wherein the lumen seal defines a space between the lumen seal and the primary lumen when the instrument is in the retracted portion, and wherein the lumen seal engages the primary lumen when the instrument is in the advanced position.

2. The instrument advancement device of claim 1, wherein the lumen seal engages a narrowed portion of the primary lumen when the instrument is in the advanced position, the narrowed portion having a smaller inner diameter than a remaining portion of the primary lumen.

3. The instrument advancement device of claim 1, wherein the lumen seal comprises a first portion and a second portion, the first portion is larger in diameter than the second portion.

4. The instrument advancement device of claim 3, wherein the lumen seal comprises a distal tapered portion.

5. The instrument advancement device of claim 1, wherein the lumen seal comprises an elastomeric material.

6. The instrument advancement device of claim 1, wherein the lumen seal defines a central opening, and wherein a portion of the instrument passes through the central opening.

7. The instrument advancement device of claim 1, wherein the instrument comprises a flow tube and a guidewire positioned distally of the flow tube.

8. The instrument advancement device of claim 7, wherein the guidewire comprises a helical coil portion.

9. The instrument advancement device of claim 7, further comprising a wedge member defining a central passage, wherein the central passage of the wedge member receives a portion of the flow tube and a portion of the guidewire, and wherein the guidewire and the flow tube are attached to the wedge member.

10. The instrument advancement device of claim 9, wherein the advancement member is configured to move along an outer surface of the primary lumen, and wherein the advancement member engages the wedge member from outside of the primary lumen to move the instrument between the retracted position and the advanced position.

11. The instrument advancement device of claim 9, wherein the lumen seal defines a central opening that receives a portion of the wedge member, and wherein the lumen seal is attached to the wedge member.

12. The instrument advancement device of claim 11, wherein the guidewire extends through the lumen seal, and wherein a portion of the flow tube is received within the central opening of the lumen seal.

13. The instrument advancement device of claim 7, wherein, when the access connector is connected to an integrated catheter, the flow tube is configured to be received within at least a portion of the integrated catheter.

14. The instrument advancement device of claim 7, wherein at least a portion of the primary lumen has an asymmetrical transverse cross-section defining a larger diameter portion and a smaller diameter portion, with a portion of the guidewire received within the smaller diameter portion.

15. The instrument advancement device of claim 14, wherein the smaller diameter portion is configured to support the guidewire when the instrument is moved from the retracted position to the advanced position.

16. The instrument advancement device of claim 1, further comprising a cannula configured to pierce the lumen seal when the instrument is moved to the advanced position, wherein a flow path defined by the instrument is sealed until the cannula pierces the lumen seal.

17. The instrument advancement device of claim 16, further comprising a vent plug positioned within the primary lumen and positioned proximally relative to the advancement member, wherein a flow path to the vent plug extends from the access connector, through the primary lumen, and between the primary lumen and the lumen seal.

18. The instrument advancement device of claim 17, wherein the vent plug comprises a hydrophilic vent and is configured to allow the primary lumen to receive a waste blood volume.

19. The instrument advancement device of claim 1, further comprising a flow restrictor configured to reduce risk of hemolysis.

20. The instrument advancement device of claim 19, wherein the flow restrictor comprises a tubular insert received within at least a portion of the access connector.

* * * * *